(12) United States Patent
Fuerst et al.

(10) Patent No.: US 8,858,466 B2
(45) Date of Patent: Oct. 14, 2014

(54) DISPOSABLE DIAGNOSTIC PART AND A METHOD FOR THE MANUFACTURE THEREOF

(75) Inventors: Otto Fuerst, Viernheim (DE); Hans-Peter Haar, Wiesloch (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 616 days.

(21) Appl. No.: 12/705,680

(22) Filed: Feb. 15, 2010

(65) Prior Publication Data

US 2010/0168617 A1 Jul. 1, 2010

Related U.S. Application Data

(63) Continuation of application No. PCT/EP2008/060780, filed on Aug. 15, 2008.

(30) Foreign Application Priority Data

Aug. 16, 2007 (EP) ..................... 07114414

(51) Int. Cl.
| | |
|---|---|
| *A61B 5/00* | (2006.01) |
| *B65D 81/00* | (2006.01) |
| *A61B 5/151* | (2006.01) |
| *A61B 5/145* | (2006.01) |
| *A61B 5/15* | (2006.01) |
| *A61B 5/1455* | (2006.01) |
| *A61B 5/1468* | (2006.01) |

(52) U.S. Cl.
CPC .............. *A61B 5/1411* (2013.01); *A61B 5/411* (2013.01); *A61B 5/15142* (2013.01); *A61B 5/14532* (2013.01); *A61B 5/1455* (2013.01); *A61B 5/1468* (2013.01)
USPC ............ 600/583; 600/573; 600/576; 600/577

(58) Field of Classification Search
USPC .................. 600/573, 576, 577, 583; 606/181
See application file for complete search history.

(56) References Cited

U.S. PATENT DOCUMENTS

| | | | | |
|---|---|---|---|---|
| 6,875,613 | B2 * | 4/2005 | Shartle et al. ................... | 436/63 |
| 6,939,312 | B2 * | 9/2005 | Hodges et al. ................ | 600/583 |

(Continued)

FOREIGN PATENT DOCUMENTS

| | | |
|---|---|---|
| EP | 0 365 196 A2 | 4/1990 |
| EP | 1 266 608 B1 | 12/2002 |
| EP | 1 464 284 B1 | 10/2004 |
| EP | 1 627 684 A1 | 2/2006 |

(Continued)

OTHER PUBLICATIONS

International Application PCT/EP2006/060780 International Search Report mailed Nov. 18, 2008.

(Continued)

*Primary Examiner* — Devin Henson
(74) *Attorney, Agent, or Firm* — Roche Diagnostics Operations, Inc.

(57) ABSTRACT

The invention concerns a disposable diagnostic part comprising a lancing element (14) which is designed for puncturing the skin (26) and has a collecting channel (16) for taking up body fluid, and comprising a detection element (18) which has a test layer (42) provided with reagents for the detection of an analyte in the body fluid and is disposed in the collecting channel (16). In order to ensure an improved stability and biocompatibility it is proposed that the detection element (18) is provided with a sealing layer (20) that is applied to the test layer (42) and covers the reagents.

28 Claims, 1 Drawing Sheet

(56) References Cited

U.S. PATENT DOCUMENTS

| | | | |
|---|---|---|---|
| 7,276,147 B2* | 10/2007 | Wilsey | 205/792 |
| 7,803,319 B2* | 9/2010 | Yang et al. | 422/423 |
| 2003/0018282 A1 | 1/2003 | Effenhauser et al. | |
| 2003/0143113 A2* | 7/2003 | Yuzhakov et al. | 422/56 |
| 2006/0079810 A1* | 4/2006 | Patel et al. | 600/583 |
| 2006/0293611 A1* | 12/2006 | Calasso et al. | 600/583 |
| 2007/0197937 A1 | 8/2007 | Sarofim et al. | |
| 2008/0249435 A1 | 10/2008 | Haar et al. | |

FOREIGN PATENT DOCUMENTS

| | | |
|---|---|---|
| WO | WO 2005/084545 A1 | 9/2005 |
| WO | WO 2007/045412 A1 | 4/2007 |
| WO | WO 2008/048709 A1 | 4/2008 |

OTHER PUBLICATIONS

International Application PCT/EP2008/060780 International Preliminary Report on Patentability mailed Mar. 11, 2010.

* cited by examiner

DISPOSABLE DIAGNOSTIC PART AND A METHOD FOR THE MANUFACTURE THEREOF

CROSS-REFERENCE TO RELATED APPLICATION

This application is a continuation of International Application No. PCT/EP2008/060780, filed Aug. 15, 2008, which claims the benefit of European Application No. 07114414.1, filed Aug. 16, 2007, the entire disclosures of which are hereby incorporated by reference.

BACKGROUND

The invention concerns a disposable diagnostic part comprising a lancing element which is designed for puncturing the skin and has a preferably laterally open collecting channel for taking up body fluid and comprising a detection element which has a test layer provided with reagents and in particular enzymes for the detection of an analyte in the body fluid and is disposed in the collecting channel. The invention additionally concerns a production process for such a disposable part.

For blood sugar self-monitoring by diabetics it is desirable to impose the fewest possible number of handling steps on the person concerned and at the same time to ensure a less painful and reliable measurement. Disposable particles are used in this connection for a skin puncture for hygienic reasons. In more recent concepts such as those which are for example described in WO 2007/045412, it is aimed to simplify the sample transfer by integrating the detection element into the disposable part in order to ensure a robust measuring process even with minimal amounts of sample.

SUMMARY

Starting from this, the object of the invention is to further improve the sample collectors and processes for their production known in the prior art and to design them such that an uncomplicated sample uptake and reliable analyte detection is made possible.

The combination of features stated in the independent patent claims is proposed to achieve this object. Advantageous embodiments and further developments of the invention are derived from the dependent claims.

The invention is based on the idea of using disposable parts in which the sample can be analysed in a biocompatible and reliable manner in a small volume as near as possible to the lancing member. Accordingly it is proposed according to the invention that the detection element integrated into the collecting channel is provided with a sealing layer which is applied to the test layer and covers the reagents. This allows the integrity of the test layer to be improved even during the assembly and storage period while at the same time ensuring that the test chemistry does not come into direct contact with the skin. Equally it can thus be ensured that no particles of solid become detached from the test layer provided with enzyme-coated dry substances and trigger allergic reactions in the body. This is of particular importance in view of the high number and necessity to repeat the application daily. The sealing also enables the detection element to be shifted distally into the lancing member so that the collecting volume can also be further reduced.

In this connection it is important that the duration of the measurement is not unacceptably elongated for the user. A preferred embodiment provides that the sealing layer is dissolvable when the collecting channel is filled by body fluid so that the analyte comes into contact with the reagents. In this case it is advantageous when the time required to dissolve the sealing layer in the body fluid is less than 10 s, preferably less than 2 s.

In order to facilitate a rapid dissolving it is advantageous when the sealing layer is designed as a liquid film or flowable fluid film.

In order to further improve protection against detachment of particles it is of particular advantage when the sealing layer encloses a margin of the detection element which borders the test layer.

In a constructionally advantageous embodiment the detection element has a support for the layers of material which are applied without having a shape of their own, where said support can be preferably made from a flat material. In this connection the test layer is located on the support and a sealing layer is provided on its side facing away from the support.

It is also advantageous when the lancing element consists of metal, in particular of steel.

In order to have as little influence as possible on the test properties and in order to optimize the layer adaptation it is advantageous when the test layer is provided with a substance that is also present in the sealing layer.

It is advantageous for the application of body fluid obtained by the lancing when the detection element is firmly inserted into an end section of the collecting channel and the test layer is aligned in the lancing direction of the lancing element.

A special aspect of the invention is that the sealing layer is formed from non-ionic surfactants. In this connection it is also conceivable that only a part of the lancing element is provided with a coating formed from non-ionic surfactants especially to improve the hydrophilicity and to create a surface which is optimized for blood uptake. In this connection it is possible that the abrasion-resistant sealing layer covers a part of the lancing element which penetrates into the skin.

Polysorbates and preferably polysorbate 20 and/or polysorbate 80 are particularly preferably used. It is also conceivable that the non-ionic surfactants contain poloxamer, preferably poloxamer 188.

Another advantageous embodiment provides that the non-ionic surfactants contain at least one substance selected from the group comprising fatty alcohol polyglycol ethers, glucamides, fatty alcohol ethoxylates, alkyl-polyglycosides, sucrose fatty acid esters.

The invention also concerns a magazine containing a plurality of disposable diagnostic parts according to the invention for use in a hand-held device especially for blood sugar determination as well as a system for analysing a body fluid, in particular as a hand-held device for blood sugar determination having at least one disposable diagnostic part according to the invention that is disposed therein or can be used therein.

With regard to the process the object mentioned above is achieved in that the lancing element and/or the detection element is at least partially coated with non-ionic surfactants as a coating material. This can be advantageously achieved in that the coating material is applied to the surface to be coated in an at least predominantly anhydrous solvent, preferably ethanol. The solvent can then be removed after the coating by a stream of gas, a vacuum and/or by heating.

The coating material is advantageously applied to the surface to be coated by means of dip coating, spray coating or contact coating. In this case it may be advantageous when the viscosity of the coating material is adjusted by additional components.

A further improvement provides that the detection element is cut out of a flat material and that the coating material is applied to the cut-out detection element before or after it is inserted into the lancing element.

For the production technology it is also advantageous when the detection element is placed on a support after the coating and in particular its front end is placed on a light guide and that subsequently the assembly unit consisting of support and detection element is assembled with the lancing element.

In order to adjust the viscosity of the coating material it is conceivable that a liquid surfactant is combined with another non-ionic (optionally also solid) surfactant provided that the resulting mixture is above all non-crystalline or flowable.

BRIEF DESCRIPTION OF THE DRAWINGS

The invention is further elucidated in the following on the basis of an embodiment example shown schematically in the drawing.

DETAILED DESCRIPTION

Figure 1:
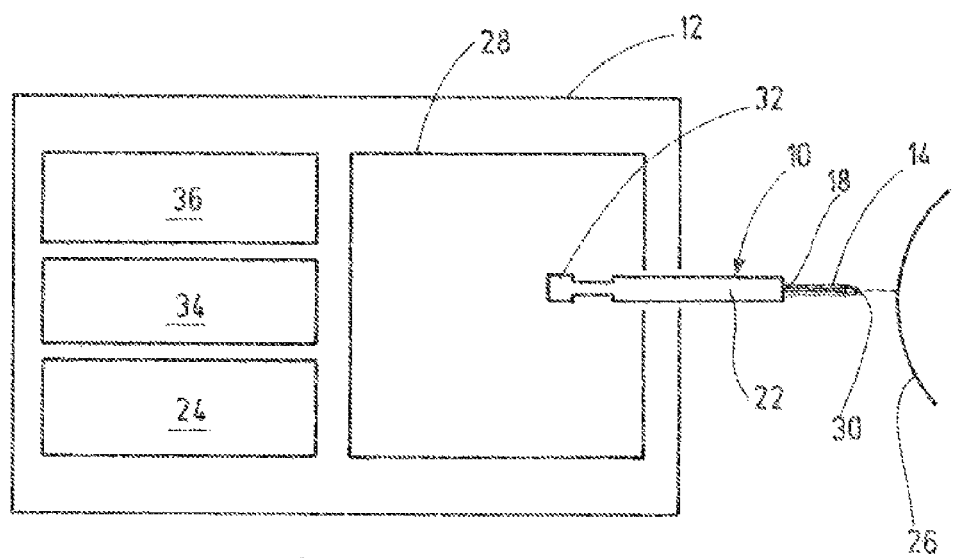
FIG. 1 shows a blood sugar measuring instrument with a microsampler inserted therein as a disposable diagnostic part in a diagrammatic representation.

The disposable diagnostic parts 10 shown in the drawing can be used as microfluidic sample collectors or microsamplers for a blood sugar determination in a hand-held device 12 designed therefor, where it is possible to carry out a glucose detection with a minimal amount of sample in the disposable part. For this purpose the microsamplers 10 comprise a lancing element 14 with a slot-shaped collecting channel 16 which is open on both sides and a detection element 18 disposed therein for an optical or electrochemical measurement directly in the collecting channel 16, where the detection element 18 and optionally also the lancing element 14 is provided with a special coating 20 made of non-ionic surfactants. A holder 22 for the lancing element and the detection element allows coupling to a lancing drive 24 for a puncture into the skin 26 for example of a finger of a user.

As shown in FIG. 1 the microsamplers 10 can be brought successively into an active application position in a magazine 28 which can be inserted into the instrument 12. In this connection the tip 30 of the active lancing element 14 points in a distal direction towards the body part 26 while a coupling end 32 of the holder 22 is coupled with the lancing drive 24 for a drive coupling and signal coupling. The body fluid (blood or tissue fluid) taken up during the skin puncture in the collecting channel 16 can be analysed directly photometrically or electrochemically by means of the detection element 18 where the signals are evaluated in an evaluation unit 34 in the instrument. In this connection it is also possible to indicate the result of the measurement to the user on a display 36 thus enabling an on-site blood sugar monitoring without complicated handling steps.

Figure 2:
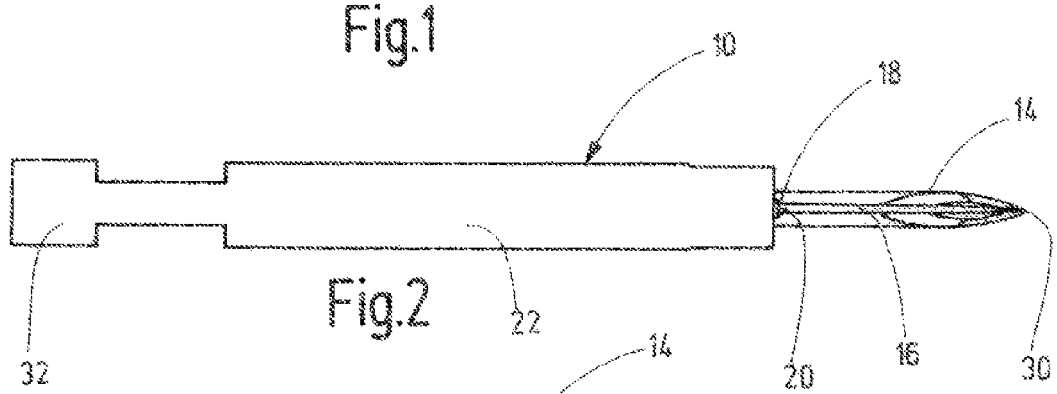
FIG. 2 shows the microsampler in a top-view of a truncated perspective representation.

As shown in FIG. 2 the shaft-shaped elongate lancing element 14 has a transverse continuous longitudinal slot as a collecting channel 16. This slot enables, optionally by means of capillary action, the transfer of a microscopic amount of liquid onto the detection element 18 which is aligned in the direction of the tip 30. The elongate slit opening that is open on both sides ensures an effective uptake of liquid without the risk of blockage by cell components. In order to withdraw blood in the gentlest possible manner with as little pain as possible it is provided that the volume of the collecting channel 16 is only a few tens of nanoliters.

Figure 3:
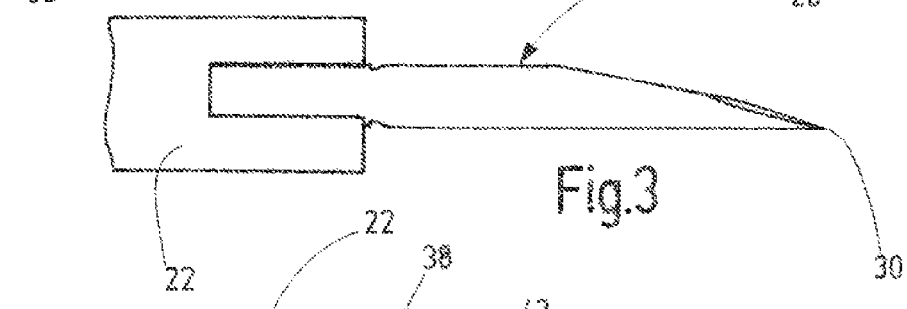
FIG. 3 shows the microsampler in a truncated side-view.

In the side view of FIG. 3 it can be seen that the proximal end of the lancing element 14 is plugged onto the holder 22 provided with lateral grooves in a clamp-like manner so that the detection element 18 which is applied to the end of the holder 22 engages in the collecting channel 16. The distal section of the lancing element 14 made of steel is ground such that it slopes towards the tip 30 in order to facilitate the skin puncture by a reduced cross-section.

Figure 4:
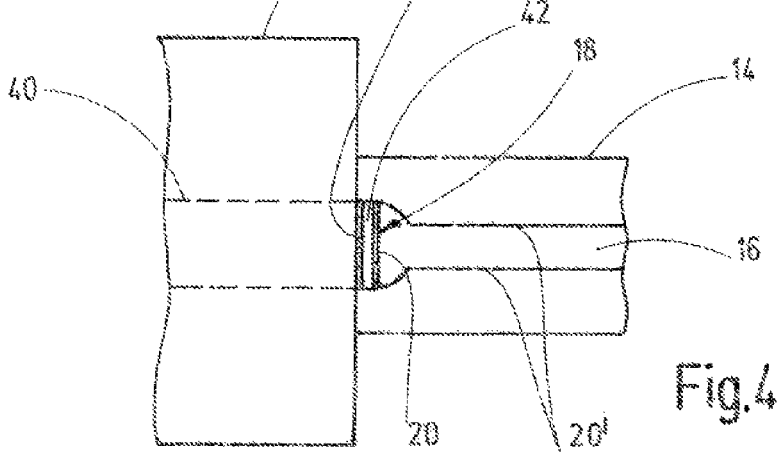
FIG. 4 shows an enlarged section of FIG. 2.

FIG. 4 shows the detection element 18 composed of several layers in an enlarged section. A transparent support 38 is provided as a base which rests on an arrangement of light guides 40 which cross the holder 22. A test layer 42 is located on the support 38 and is provided with reagents for a glucose detection in the blood fluid collected in the collecting channel 16 and optionally further auxiliary substances. The reagents can consist of a known enzymatic system which reacts irreversibly with glucose with a colour change but do not dissolve in the blood fluid. An optical detection by the instrument is enabled by means of scattering particles within the chemistry system with back-scattering of the measuring light that is radiated in via the arrangement of light guides 40.

The sealing layer 20 covers the test layer 42 and thus seals the reagents so that firstly a good storage stability is achieved and reagent particles are prevented from detaching from the dry-stored test surface. The sealing also results in an important user advantage in that it prevents direct skin contact with the test surface or with substances that are detached therefrom during the puncture. The sealing layer 20 also advantageously encloses the margins of the test area 42 in order to reliably prevent a detachment of particles. This is particularly important when the detection element 18 is made by cutting it from a large area of coated foil material.

In order to not significantly impair the detection of the analyte, the sealing layer 20 is dissolvable when blood fluid which flows into the collection channel 16 is applied thereto. The time required for an adequate dissolution i.e. the time until a measurement signal that can be analysed is obtained should be less than 2 seconds in order not to limit the user convenience. Accordingly the sealing layer 20 should have a high hydrophilicity where a liquid film design is advantageous.

It goes without saying that the sealing layer 20 should be biocompatible so that it does not itself trigger disadvantageous reactions upon skin contact. This can be achieved in a particularly reliable manner by using pharmacologically approved harmless substances as well as harmless substances that are approved for food chemistry as a coating material. However, such substances should not have independent pharmacological functional properties within the scope of the pharmacological registration.

Finally the coating material should not have an effect on the test reagents and the test process and thus on the result, regardless of whether a contact with the test surface takes place during production, storage or not until sample measurement. Ideally an existing test chemistry should not only be compatible with regard to the coating material but should also advantageously itself contain this material as the test area 42. Thus, the test area 42 can contain that substance which is also used as a sealing material, as a wetting agent which is in any case required. In this manner critical concentration gradients or disadvantageous changes in the overall system are avoided.

A coating 20' of the lancing element 14 can also prove to be advantageous in order to create a hydrophilic surface for the uptake of body fluid especially in the area of the collecting channel 16. It is also possible to reduce the friction during lancing and thus the lancing pain by means of a coating in the area of the tip 30.

In this connection non-ionic surfactants and above all polysorbates have proven to be a particularly suitable coating material for fulfilling the aforementioned requirements and enabling a mass production of disposable articles in a practical manner. Polysorbate 20 (PS 20) which has the following advantages is particularly preferably used:

PS 20 is used in pharmaceutical preparations (injection solutions) and is also found in foods.

PS 20 can be stored for a long period and is still active even long after the expiry date.

PS 20 has a high molecular weight and thus hardly diffuses through body tissue.

PS 20 is viscous at room temperature and dissolves well in the solvent ethanol (and not only in water).

PS 20 is sterile in the solvent ethanol, does not become contaminated with microorganisms and wetted areas are sterilized by the solvent.

PS 20 can be easily applied in an ethanolic solution and rapidly and readily penetrates into capillary structures due to the low solvent viscosity.

PS 20 applied from ethanol can be rapidly and reliably freed from ethanol (e.g. by a stream of air or a vacuum).

PS 20 does not form a crystal lattice and consequently rapidly dissolves on contact with the water of the sample (blood) because a high enthalpy of solution is not required to overcome lattice forces. A rapid interaction with the sample also leads to a rapid wetting.

PS 20 also creeps (depending on the amount) into the finest structures after drying. The hydrophilicity and wetting rate appears to become even better and not poorer after some storage time.

PS 20 did not exhibit a detectable effect on the detection reaction in the initial experiments.

PS 20 should inhibit coagulation to a slight extent but not in a functional manner (and indeed only in the collecting channel, whereas outside the channel the dilution is too high).

The consistency or viscosity of PS 20 can, if necessary, be optimized by adding other components. For example an addition of poloxamer 188 (solid) can suitably modify the creep capability of PS 20. Polysorbate 80 has also proven to be a suitable coating material.

The following detergents are further conceivable classes of substances which, although being foreign to the body, are nevertheless used in food chemistry and biochemistry or molecular biology:

AEOs: fatty alcohol polyglycol ethers $CH_3$—$(CH_2)_{16}$—$CH_2$—$(OCH_2CH_2)_n$—OH n=1-20 glucamides, derived from fatty acids and glucose R—CO—NH—$CH_2$—$(CH_2)_4$—$CH_2$—OH R=$C_{11}H_{23}$ fatty alcohol ethoxylates APGs (alkyl-polyglycosides) polyglycosil-O—$(CH_2)_n$—$CH_3$ n=e.g. 12 sucrose fatty esters (sucrose: glucose-$C_6$)-O—CO—$(CH_2)_n$—$CH_3$ n=10-16

Of course combinations of these substances with one another or with other substances are conceivable.

Hence, when producing disposable diagnostic articles 10 it is advantageous that the lancing element 14 and/or the detection element 18 is at least partially coated with non-ionic surfactants as a coating material. This can be achieved by applying the coating material to the surface to be coated by dip coating, spray coating or contact coating. The coating material is advantageously applied to the surface to be coated in ethanol as a solvent and subsequently the solvent is removed for example by a stream of gas, a vacuum and/or heating.

The detection element 18 as a cut-out piece of flat material can be attached after coating to the support 22 i.e. with its front end on the light guide 40 and subsequently the assembly unit consisting of support 22 and detection element 18 are assembled with the lancing element 14. Further details on this are given by the patent application PCT/US07/65918 to which reference is expressly made in this connection.

The invention claimed is:

1. Disposable diagnostic part comprising a lancing element which is designed for puncturing the skin and has a laterally open collecting channel for taking up body fluid, and comprising a detection element which has a test layer provided with reagents for the detection of an analyte in the body fluid and is disposed in the collecting channel, characterized in that the detection element is provided with a sealing layer which is applied to the test layer and covers the reagents, wherein the sealing layer is distinct from the reagents, wherein the sealing layer is disposed in the collecting channel, wherein the sealing layer seals the reagents from an outside environment and prevents particles of reagent detaching from the test layer, wherein the lancing element has a tip for puncturing the skin, wherein the sealing layer is provided over the test layer and is located between the reagent and the tip.

2. Disposable diagnostic part according to claim 1, characterized in that the sealing layer is dissolvable when the collecting channel is filled by body fluid so that the analyte comes into contact with the reagents.

3. Disposable diagnostic part according to claim 1, characterized in that the time required to dissolve the sealing layer in the body fluid is less than 10 s.

4. Disposable diagnostic part according to claim 3, wherein the time required to dissolve the sealing layer in the body fluid is less than 2 s.

5. Disposable diagnostic part according to claim 1, characterized in that the sealing layer is in the form of a liquid film.

6. Disposable diagnostic part according to claim 1, characterized in that the sealing layer encloses a margin of the detection element which borders the test layer.

7. Disposable diagnostic part according to claim 1, characterized in that the detection element has a support formed from a flat material.

8. Disposable diagnostic part according to claim 1, characterized in that the lancing element consists of metal.

9. Disposable diagnostic part according to claim 1, characterized in that the test layer is provided with a substance that is also present in the sealing layer.

10. Disposable diagnostic part according to claim 8, wherein the metal includes steel.

11. Disposable diagnostic part according to claim 1, characterized in that the detection element is firmly inserted into an end section of the collecting channel and the test layer is aligned in the lancing direction of the lancing element.

12. Disposable diagnostic part according to claim 1, characterized in that the sealing layer is formed from non-ionic surfactants.

13. Disposable diagnostic part according to claim 1, wherein the reagents include enzymes.

14. Disposable diagnostic part according to claim 1, wherein the sealing layer is positioned transverse to a flow direction of the body fluid in the collecting channel.

15. Disposable diagnostic part comprising a lancing element which is designed for puncturing the skin and has a laterally open collecting channel for taking up body fluid, and comprising a detection element which has a test layer provided with reagents for the detection of an analyte in the body fluid, characterized in that the detection element is at least partially provided with a sealing layer formed from non-ionic surfactants, wherein the sealing layer is distinct from the test layer, wherein the sealing layer completely covers the test layer such that a margin surrounding the test layer is covered by the sealing layer to prevent detachment of particles of the reagent, wherein the sealing layer is located so that the body fluid contacts the sealing layer before contacting the test layer, wherein the sealing layer is dissolvable when the collecting channel is filled by body fluid so that the analyte comes into contact with the reagents.

16. Disposable diagnostic part according to claim 15, characterized in that the non-ionic surfactants contain a polysorbate.

17. Disposable diagnostic part according to claim 16, wherein the polysorbate includes polysorbate 20.

18. Disposable diagnostic part according to claim 17, wherein the polysorbate includes polysorbate 80.

19. Disposable diagnostic part according to claim 16, wherein the polysorbate includes polysorbate 80.

20. Disposable diagnostic part according to claim 15, characterized in that the non-ionic surfactants contain poloxamer.

21. Disposable diagnostic part according to claim 20, wherein the poloxamer includes poloxamer 188.

22. Disposable diagnostic part according to claim 15, characterized in that the non-ionic surfactants contain at least one substance selected from the group comprising fatty alcohol polyglycol ethers, glucamides, fatty alcohol ethoxylates, alkyl-polyglycosides, sucrose fatty acid esters.

23. Disposable diagnostic part according to claim 15, characterized in that the sealing layer covers a part of the lancing element which penetrates into the skin.

24. Disposable diagnostic part according to claim 15, characterized in that the sealing layer forms a hydrophilic surface for the uptake of body fluid during skin puncture.

25. Magazine for holding a plurality of disposable diagnostic parts according to claim 15 for use in a hand-held device especially for the determination of blood sugar.

26. System for analysing a body fluid in particular as a hand-held device for determining blood sugar comprising at least one disposable diagnostic part according to claim 15 which is disposed therein or can be inserted therein.

27. Disposable diagnostic part according to claim 15, wherein the reagents include enzymes.

28. Disposable diagnostic part according to claim 15, wherein the sealing layer is positioned transverse to a flow direction of the body fluid in the collecting channel.

* * * * *